United States Patent [19]

Tomic

[11] Patent Number: 4,678,670

[45] Date of Patent: Jul. 7, 1987

[54] PHARMACEUTICAL COMPOSITIONS FOR THE TREATMENT OF DIABETES AND OF HEPATIC DISEASES AND MALFUNCTIONS

[76] Inventor: Dobrivoje Tomic, 11, Dell'Oro Street, Caldaro (Bolzano), Italy

[21] Appl. No.: 698,406

[22] Filed: Feb. 5, 1985

[30] Foreign Application Priority Data

Feb. 17, 1984 [IT] Italy .................................. 19681 A/84

[51] Int. Cl.⁴ .............................................. A61K 31/00
[52] U.S. Cl. ................................. 424/127; 424/154; 514/866; 514/894
[58] Field of Search ................................ 514/127, 154

[56] References Cited

U.S. PATENT DOCUMENTS 4,448,770 5/1984 Epting .................................. 424/154
4,544,550 10/1985 Rodolfo .............................. 424/127

*Primary Examiner*—Frederick E. Waddell
*Attorney, Agent, or Firm*—Bucknam and Archer

[57] ABSTRACT

Pharmaceutical compositions for the treatment of diabetes and hepatitis of various nature and, generally, of hepatic malfunctions, comprising a combination of (a) an alkali or alkali-earth metal nitrate, (b) a carbohydrate and, optionally, (c) a per se known hepato-protecting agent.

6 Claims, No Drawings

PHARMACEUTICAL COMPOSITIONS FOR THE TREATMENT OF DIABETES AND OF HEPATIC DISEASES AND MALFUNCTIONS

The invention refers to pharmaceutical compositions suited for the treatment of diabetes and hepatic diseases and malfunctions, and for the enhancement of the hepatic functions, the compositions being constituted by a combination of (a) an alkali or alkaline earth metal nitrate, (b) a sugar and optionally a per se known hepatoprotective agent. Several therapeutic agents are known for the treatment of diseases and hepatic malfunctions: for example, silymarin; thiopronine; arginine or bethaine aspartate; dehydrocholic acid; thioctic acid; compositions containing glucocorticoids, folic acid, cyanocobalamine and other vitamins. Some of these agents exhibit adverse side-effects; other ones are endowed with very low activity; finally, a drawback common to most of them is the need of a very prolonged treatment.

New pharmaceutical compositions have now been found for the treatment of diabetes, of hepatic diseases and for restoring the normal hepatic functions, characterized by a very fast action, an excellent tolerability and the lack of adverse side-effects.

The pharmaceutical compositions according to the invention are constituted by:
(a) one or more alkali or alkaline earth metal nitrates;
(b) one or more edible sugars;
(c) optionally, a per se known hepatoprotective agent.

The single components (a) and (b), and optionally (c), are present in the compositions in established ratios.

Moreover, the compositions according to the invention can comprise vitamins, particularly of the B group.

As component (a), sodium, potassium, calcium, magnesium nitrate are particularly suited; sodium nitrate is particularly preferred.

As component (b) monosaccharides, disaccharides or polysaccharides such as erhythrose, threose, arabinose, xylose, glucose, fructose, mannose, galactose, saccharose, lactose, pectines, starch, are suited; saccharose, especially not completely refined (so called "cane sugar"), is particularly preferred.

The two components (a) and (b) can be present in the pharmaceutical compositions according to the invention in weight ratios ranging from 1:10 to 10:1, preferably from 1:5 to 5:1 and even more preferably from 1:3 to 3:1. The compositions object of the invention may be in form of tablets, powders, capsules, syrups and so on, and containing excipients, solvents, adjuvants etc., commonly known in pharmaceutical preparations.

Non limitative examples of pharmaceutical compositions according to the invention are reported hereinafter.

EXAMPLE 1

A mixture of 1 part by weight of very pure sodium nitrate and 2 parts by weight of "cane sugar" is finely ground. The obtained powder is distributed into capsules weighing 1 g or 2 g each, or in cachets containing 5 g of said powder; alternatively, it may be administered by means of spoons, tea-spoons or coffee-spoons.

EXAMPLE 2

The same method of Example 1 is followed substituting sodium nitrate with an equivalent amount (1.18 parts by weight) of extra pure potassium nitrate.

EXAMPLE 3

The same method of Example 1 is used, substituting "cane sugar" with an equal amount of lactose.

EXAMPLE 4

The following compounds are homogeneously mixed:
35 g of extra pure $NaNO_3$
70 g of "cane sugar";
0.4 g of vitamin $B_1$;
0.4 g of vitamin $B_2$;
0.4 g of vitamin $B_6$;
0.15 g of vitamin $B_{12}$.

Capsules or tablets weighing 1 or 2 g or cachets weighing 5 g are prepared with the so obtained mixture.

EXAMPLE 5

10 Grams of silymarine or 20 g of thiopronine or 2.5 g of dehydrocholic acid are added to the mixture according to Example 4.

EXAMPLE 6

The method according to Example 4 is used substituting the sodium nitrate with 41.5 g of extra pure $KNO_3$, or with 48.5 g of $Ca(NO_3)_2.4H_2O$.

EXAMPLE 7

A syrup is prepared from the mixture described in Example 4 by addition of bidistilled water to a total of 200 ml.

EXAMPLE 8

A syrup as in Example 7 is prepared, by substituting the "cane sugar" with an equal amount of common sugar, or glucose, or, honey.

The efficacy of the pharmaceutical compositions according to the invention is clearly shown mainly from the results obtained in the treatment of viral hepatitis and diabetes.

It is known that, in the hepatitis, as in all the other instances of hepatic parenchyma damage, an increase of the serum enzymatic activity takes place, probably due to the release of enzymes from the impaired hepatic cells. The most frequently controlled enzymes in case of hepatic diseases are transaminases, mainly the so called SGOT (Serum-glutamate-oxalacetate-transaminase) and SGPT (Serum-glutamate-pyruvate-transaminase). The latter is particularly specific for hepatic damages.

While in a normal hepatic situation the SGOT and SGPT values oscillate from 15 to 18 UI, in the case of acute hepatitis the transaminases rise to 100–500 UI and over 1000 UI when hepatic Jaundice or coma is reached.

31 Patients, affected by acute viral hepatitis, have been treated with the compositions according to the invention; 26 patients were 26–34 years old, the remaining five patients were more than 70 years old. The transaminases values ranged from 500 to 1000 in most cases (28 patients), higher than 1000 in the remaining three cases (hepatic coma). 10 Grams/day (divided in two doses) of the composition according to the Example 1 were administered to the patients. The transaminases values rapidly decreased, being reduced to one half in 3-4 days and achieving the normality in about 8 days. In the case of hospitalization, the patients were considered clinically recovered, and discharged, 8 days after the start of treatment.

All the 31 patients recovered, without any side-effect. The first treatments have been carried out more than 10 years ago, and also in these cases periodical controls did now show either relapses or side-effects.

Various other tens of patients, affected by chronic hepatitis of minor seriousness in comparison with those described above, have been treated with complete success by administering 2-5 g/day of the compositions according to the invention for 10-15 days.

As far as diabetes is concerned, 9 patients, 22-56 years old, affected by diabetes since 3-20 years, and usually subjected to suitable diet and insulin therapy, were treated with the compositions according to Example 1 in amounts of 5 g/day, administered in a morning single dose, for twenty days, in fasting conditions.

In all the cases the glycemia values turned out to be normalized 6 weeks after the start of the treatment.

Particularly, a patient of 33 years old, diabetic since 5 years with usual glycemia around 180 mg/100 ml, was subjected to "glucose stimulus", i.e. to administration of 100 g of glucose dissolved in water, in the morning and in fasting conditions, only once, before the treatment with the composition of Example 1 and 6 weeks after the start of treatment.

The following Table reports the glycemia values at different times from the ingestion.

| Time | Before treatment | After treatment |
|------|------------------|-----------------|
| 0    | 126              | 89              |
| 30'  | 229              | 184             |
| 60'  | 216              | 224             |
| 90'  | 185              | 165             |
| 120' | 166              | 103             |

Another patient (56 years, suffering from diabetes since at least 20 years) with usual glycemia ranging from 180 to 300 mg/100 ml in spite of strict diet and strong therapy, had a decrease of the glycemia to 115-118 six weeks after the start of the treatment.

Perfectly consistent results were obtained with the other seven patients.

I claim:

1. A pharmaceutical composition for the therapy of diabetes and viral hepatitis and malfunctions which consists of component (a) sodium nitrate; component (b) which is a monosaccharide or a disaccharide which is cane sugar, saccharose, lactose, glucose or honey; the ratio of component (a) and (b) being in the ratio of 1:3-3:1 and at least one excipient.

2. The composition according to claim 1 which consists of one part of sodium nitrate and two parts of cane sugar.

3. The method of treating a patient affected by viral hepatitis or diabetes which consists of administering to said patient an effective amount of a composition consisting of sodium nitrate and at least one of cane sugar, saccharose, lactose, glucose or honey.

4. The method of treating a patient affected by viral hepatitis or diabetes which consists of administering to said patient an effective amount of a composition consisting of sodium nitrate and at least one of cane sugar, saccharose, lactose, glucose or honey, and additionally contains an hepatoprotective agent which is a member selected from the group consisting of sylimarin, thiopronin, dehydrocholic acid, arginine, betaine aspartates, thioctic acid, folic acid, glucocorticoids and mixtures thereof.

5. A pharmaceutical composition according to claim 1 which contains 0.4 grams of each of vitamin $B_1$, Vitamin $B_2$, Vitamin $B_6$ and 0.15 grams of Vitamin $B_{12}$ and the composition contains 35 grams of sodium nitrate and 70 grams of cane sugar.

6. A pharmaceutical composition according to claim 1 in the form of a powder, a tablet, a capsule or a syrup.

* * * * *